US010682487B2

(12) United States Patent
Le

(10) Patent No.: US 10,682,487 B2
(45) Date of Patent: Jun. 16, 2020

(54) SCENT DELIVERY ADAPTOR FOR CPAP

(71) Applicant: Son Q. Le, Orem, UT (US)

(72) Inventor: Son Q. Le, Orem, UT (US)

(73) Assignee: CPAP Infusion, LLC, Orem, UT (US)

(*) Notice: Subject to any disclaimer, the term of this patent is extended or adjusted under 35 U.S.C. 154(b) by 413 days.

(21) Appl. No.: 14/616,709

(22) Filed: Feb. 8, 2015

(65) Prior Publication Data

US 2018/0008796 A1 Jan. 11, 2018

(51) Int. Cl.
*A61M 16/14* (2006.01)
*A61M 16/00* (2006.01)
*A61M 16/06* (2006.01)
*A61M 16/08* (2006.01)
*A61M 21/00* (2006.01)

(52) U.S. Cl.
CPC ...... *A61M 16/142* (2014.02); *A61M 16/0057* (2013.01); *A61M 16/06* (2013.01); *A61M 16/0816* (2013.01); *A61M 21/00* (2013.01); *A61M 2021/0016* (2013.01); *A61M 2202/0468* (2013.01); *A61M 2205/123* (2013.01)

(58) Field of Classification Search
CPC .......... A61M 16/142; A61M 21/02; A61M 2021/0016; A61M 16/0057; A61M 16/06; A61M 16/0816; A61M 21/00; A61M 2202/0468; A61M 2205/123; A61M 16/10; A61M 16/14; A61M 31/00; A61M 31/002; A61M 39/00; A61F 9/04
USPC .................................................. 128/204.13
See application file for complete search history.

(56) References Cited

U.S. PATENT DOCUMENTS

| | | | | | |
|---|---|---|---|---|---|
| 4,356,969 | A | * | 11/1982 | Obermayer | A01M 1/2044 239/56 |
| 6,167,883 | B1 | * | 1/2001 | Beran | F16L 53/38 128/203.17 |
| 6,698,665 | B2 | * | 3/2004 | Minamite | A45D 34/02 239/211 |
| 7,726,309 | B2 | * | 6/2010 | Ho | A61M 16/08 128/204.18 |
| 8,668,885 | B2 | * | 3/2014 | Wirz | A61L 9/03 239/44 |
| 9,144,654 | B2 | * | 9/2015 | Kwok | A61F 5/56 |
| 9,925,351 | B2 | * | 3/2018 | Keener | A61M 15/08 |
| 2007/0193577 | A1 | * | 8/2007 | Keller | A61K 9/0078 128/200.14 |
| 2008/0196711 | A1 | * | 8/2008 | Duncan | A61M 16/16 128/200.14 |
| 2009/0145434 | A1 | * | 6/2009 | Herrmann | A61M 16/06 128/203.29 |

(Continued)

*Primary Examiner* — Jan Christopher L Merene
*Assistant Examiner* — Brian M. Booker
(74) *Attorney, Agent, or Firm* — Workman Nydegger

(57) ABSTRACT

Embodiments of an adaptor for delivering diffused aromatic agents to a user of a CPAP machine is disclosed in this document. The adaptor may include a connector body, a diffuser pad disposed within the connector body, and at least one coupling mechanism on the connector body coupling the connector body within the air supply and positioning the diffuser pad within the airflow of a CPAP machine. The adaptor may be configured to couple directly to a CPAP mask. Similarly, the adaptor may be configured to be placed in the airflow between the CPAP air generator and the mask. The adaptor may be configured such that no modification of the existing CPAP hose, machine, or mask is required.

20 Claims, 5 Drawing Sheets

(56) References Cited

U.S. PATENT DOCUMENTS

| | | | | |
|---|---|---|---|---|
| 2010/0022819 A1* | 1/2010 | Randall | ................ | A61M 11/041 |
| | | | | 600/27 |
| 2013/0233318 A1* | 9/2013 | Graham | ................ | F16L 53/38 |
| | | | | 128/205.27 |
| 2013/0263858 A1* | 10/2013 | Ho | ................ | A61M 16/0683 |
| | | | | 128/205.25 |
| 2013/0312749 A1* | 11/2013 | Bornn | ................ | A61M 16/06 |
| | | | | 128/203.29 |
| 2014/0182592 A1* | 7/2014 | Aharoni | ............ | A61M 16/0045 |
| | | | | 128/205.25 |
| 2014/0336565 A1* | 11/2014 | Nichols | ................ | A61M 11/005 |
| | | | | 604/24 |
| 2015/0245621 A1* | 9/2015 | Stewart | ................ | A01N 65/28 |
| | | | | 2/243.1 |
| 2016/0113817 A1* | 4/2016 | Chen | ................ | A61F 9/04 |
| | | | | 2/15 |
| 2017/0080038 A1* | 3/2017 | Botzem | ................ | A61K 36/53 |
| 2018/0008796 A1* | 1/2018 | Le | ................ | A61M 16/142 |
| 2018/0028776 A1* | 2/2018 | Clark | ................ | A61M 21/02 |
| 2018/0072495 A1* | 3/2018 | Langlotz | ................ | B65F 1/0026 |

\* cited by examiner

SCENT DELIVERY ADAPTOR FOR CPAP

FIELD

This application relates generally to CPAP (continuous positive airway pressure) devices. In particular, this application relates devices that introduce vapors into the airway of a CPAP machine.

BACKGROUND

Many millions of people around the globe suffer from sleep apnea. Many of those rely on CPAP machines to sleep well. CPAP machines help to maintain a positive supply of air while sleeping. Some CPAP machines include additional functions such as humidifiers and diffusers for a variety of purposes.

In recent years, sales for aromatic oils, perfumes, and other similar things have exploded. Particularly, essential oils used with diffusers for pleasure and therapeutic purposes have become a major market success. Essential oils, known as nature's living energy, are the natural, aromatic volatile liquids found in shrubs, flowers, trees, resins, fruit peels, rhizomes, roots, bushes, and seeds. The distinctive components in essential oils defend plants against insects, environmental conditions, and disease. They are also vital for a plant to grow, live, evolve, and adapt to its surroundings. Essential oils are extracted from aromatic plant sources via steam distillation, cold pressing, and other types of distillation. Essential oils are highly concentrated and far more potent than dry herbs.

While essential oils often have a pleasant aroma, their phytochemical makeup is complex and their benefits vast, which makes them much more than something that simply smells good. Historically, essential oils have played a prominent role in everyday life, Today, essential oils are used for aromatherapy, massage therapy, emotional health, personal care, nutritional supplements, household solutions, and much more. The primary methods of using essential oils include inhalation and topical application. Diffusers and humidifiers can be used to disperse oils into the air for inhalation.

SUMMARY

Accordingly, embodiments are described herein that provide an adaptor for delivering diffused aromatic agents to a user of a CPAP machine. The adaptor may include a connector body, a diffuser pad disposed within the connector body, and at least one coupling mechanism on the connector body coupling the connector body within the air supply and positioning the diffuser pad within the airflow of a CPAP machine. The adaptor may be configured to couple directly to a CPAP mask. Similarly, the adaptor may be configured to be placed in the airflow between the CPAP air generator and the mask. The adaptor may be configured such that no modification of the existing CPAP hose, machine, or mask is required.

In some embodiments, essential oils may be permeated into the pad. The pad may be formed of polyester felt, or another wicking material. The connector body may include a hose attachment and a mask attachment. Similarly, the at least one coupling mechanism may include a tube formed of a pliable material such as silicone rubber, rubber, vinyl, etc.

The aromatic agents may be diffused into the air supply of a CPAP machine by providing a CPAP machine having an air generator, a supply hose, and a mask, and inserting an adaptor between the air generator and the mask. The pad may be impregnated with the aromatic agents prior to using the CPAP machine. The aromatic agents may be essential oils. The pad may be generally planar and held within the airflow between the air generator and the mask by the adaptor. Similarly, the pad may be held parallel to the direction of the airflow such that the airflow passes over the surface of the pad.

BRIEF DESCRIPTION OF THE DRAWINGS

The following description can be better understood in light of Figures, in which.

Figure 1:
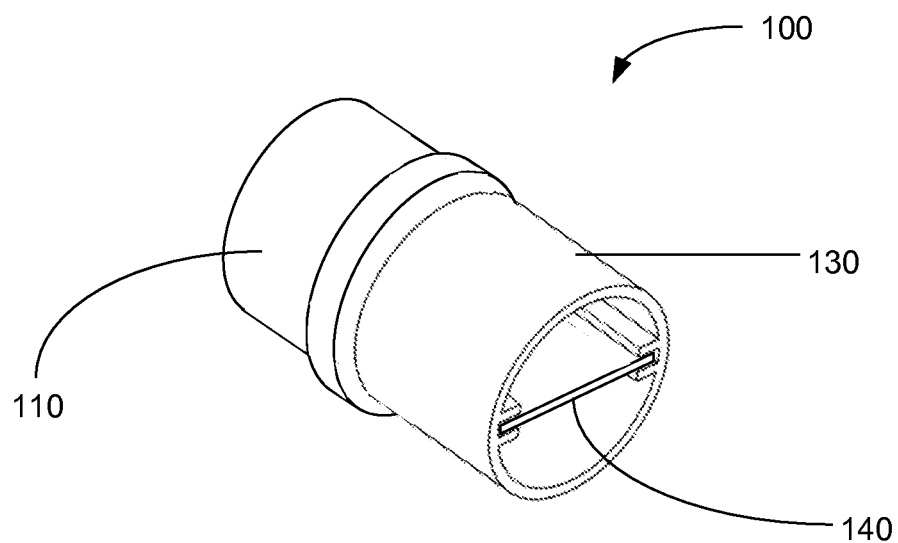
FIG. 1 is an isometric view of an exemplary embodiment of a scent delivery adaptor.

Together with the following description, the Figures demonstrate and explain the principles of scent delivery adaptors for CPAP machines and methods of making and using the same. In the Figures, the thickness and configuration of components may be exaggerated for clarity. The same reference numerals in different Figures represents the same component.

DETAILED DESCRIPTION

The following description supplies specific details in order to provide a thorough understanding. Nevertheless, the skilled artisan would understand that the apparatus and associated methods of using the apparatus can be implemented and used without employing these specific details. Indeed, the apparatus and associated methods can be placed into practice by modifying the illustrated apparatus and associated methods and can be used in conjunction with any other apparatus and techniques conventionally used in the industry. For example, while the description below focuses on a two-piece adaptor, an adaptor of unitary construction may be accomplished.

Embodiments of adaptors for delivering scents and vapors through diffusion in a CPAP machine, along with methods of making and using the same are described below in detail. In particular, the Figures provide details of specific exemplary embodiments which illustrate particular details of such adaptors. CPAP machines generally include a pressure or air generator 40 attached via a hose 20 to a mask 10 that a user wears. The user generally wears the mask 10 when sleeping to help maintain an open airway, resulting in more restful sleep and increased blood oxygenation.

In the embodiments described below, scents or other aromatic agents may be placed on a pad, which may be situated in the airway between the CPAP pressure generator and the CPAP mask. The aromatic agents may then actively diffuse into the airflow into the mask to be breathed by the user. Various essential oils, some of which may have various desirable health benefits, may be used to help with sleep, provide a pleasant aromatic experience, aroma therapy, or to address specific health issues of a user.

Figure 2:
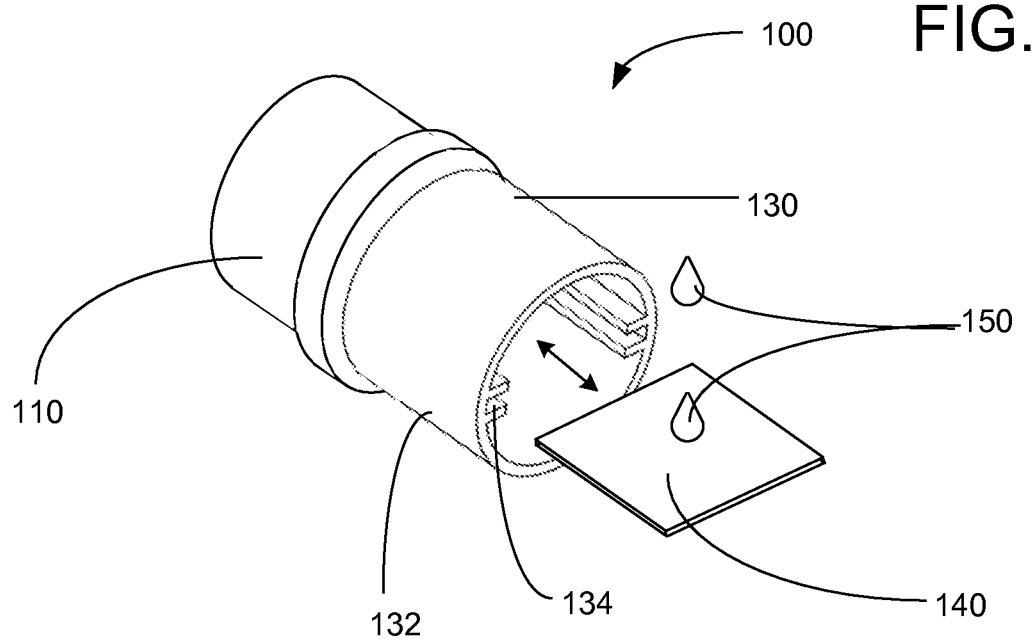
FIG. 2 is an isometric view of aromatics being applied to the scent delivery adaptor of FIG. 1.
Figure 3:
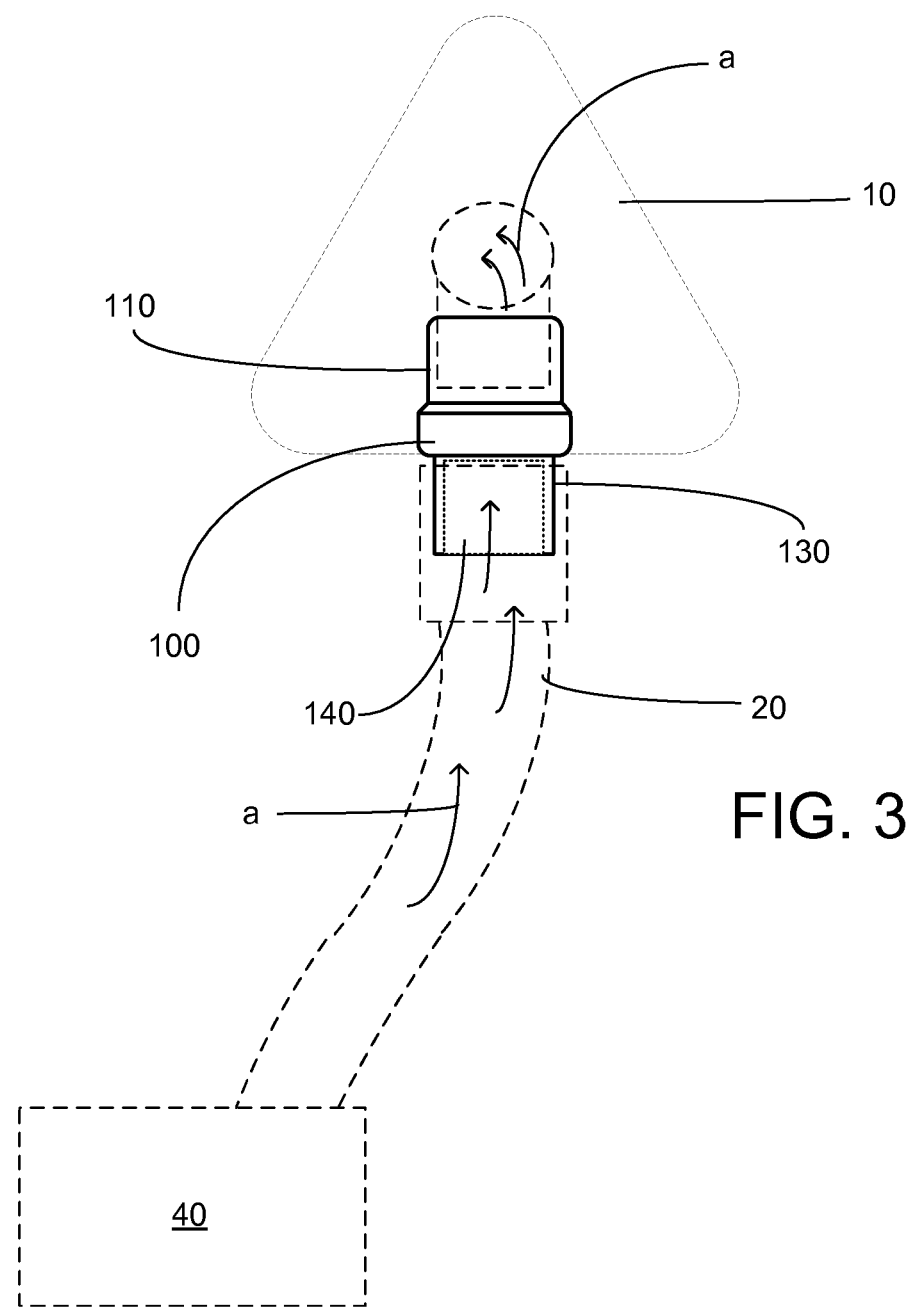
FIG. 3 shows an exemplary embodiment of scent delivery adaptor in use with a CPAP mask.
Figure 4:
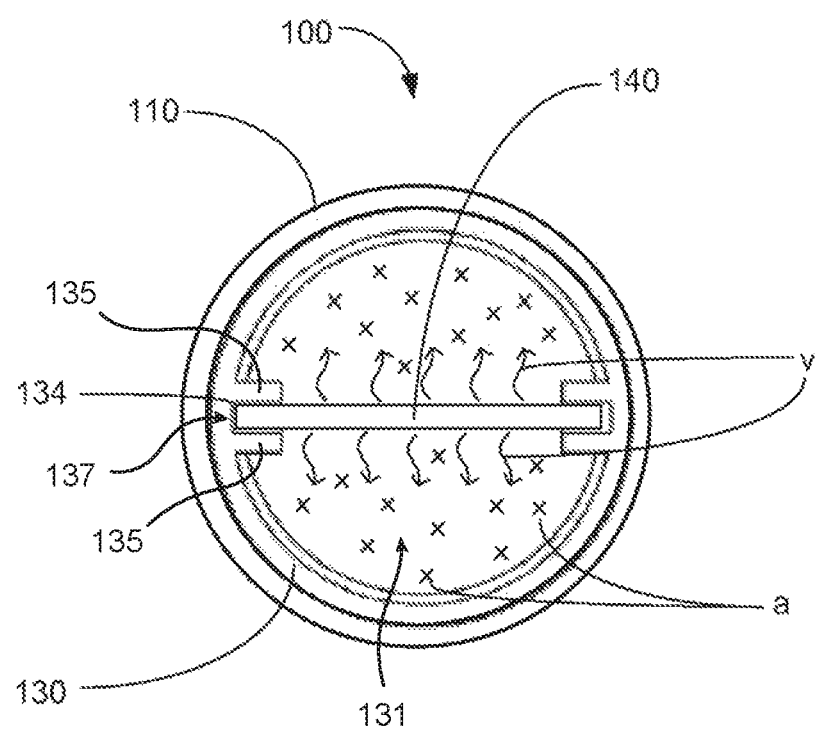
FIG. 4 shows an exemplary embodiment of the process of scent delivery through the scent delivery adaptor of FIG. 1.

Turning now to the embodiments shown in FIG. 1, adaptor 100 may include a mask connector 110, a hose connector 130, and a diffuser pad 140. The specific details of each piece will be addressed below in turn. FIGS. 2-4 in particular, illustrate the functionality of adaptor 100.

Starting with FIG. 2, the method of using and the functionality of adapter 100 will be explained. Pad 140 may be removed from retaining slot 134 formed in hose connector 130 for holding pad 140 in place during use. A desired amount of aromatic drops 150 may be applied to pad 140, and pad 140, now impregnated with aromatic drops 150, may then be placed inside of hose adaptor 130 and secured in place by placing pad 140 in slot 134. As shown in FIG. 3, adaptor 100 may then be placed in the airstream a of a CPAP machine between mask 10 and hose 20. In other embodiments, adaptor 100 may be placed anywhere between pressure generator 40 and mask 10. As shown in FIG. 4, airflow a moving past pad 140 may carry vapors v along the airpath, to mask 10, and made available to be breathed by a user. The movement of airflow a across pad 140 creates a convective effect causing additional vaporization of the aromatic drops that were applied to pad 140 when compared to static vaporization. The amount of vapors made available and the duration of the aroma may depend on the composition of pad 140, the amount of aromatic drops 150 applied, the volume of air being supplied through hose 20, the humidity and pressure of the air supplied, and the volatility of the aromatic drops applied to pad 140.

Figure 5:
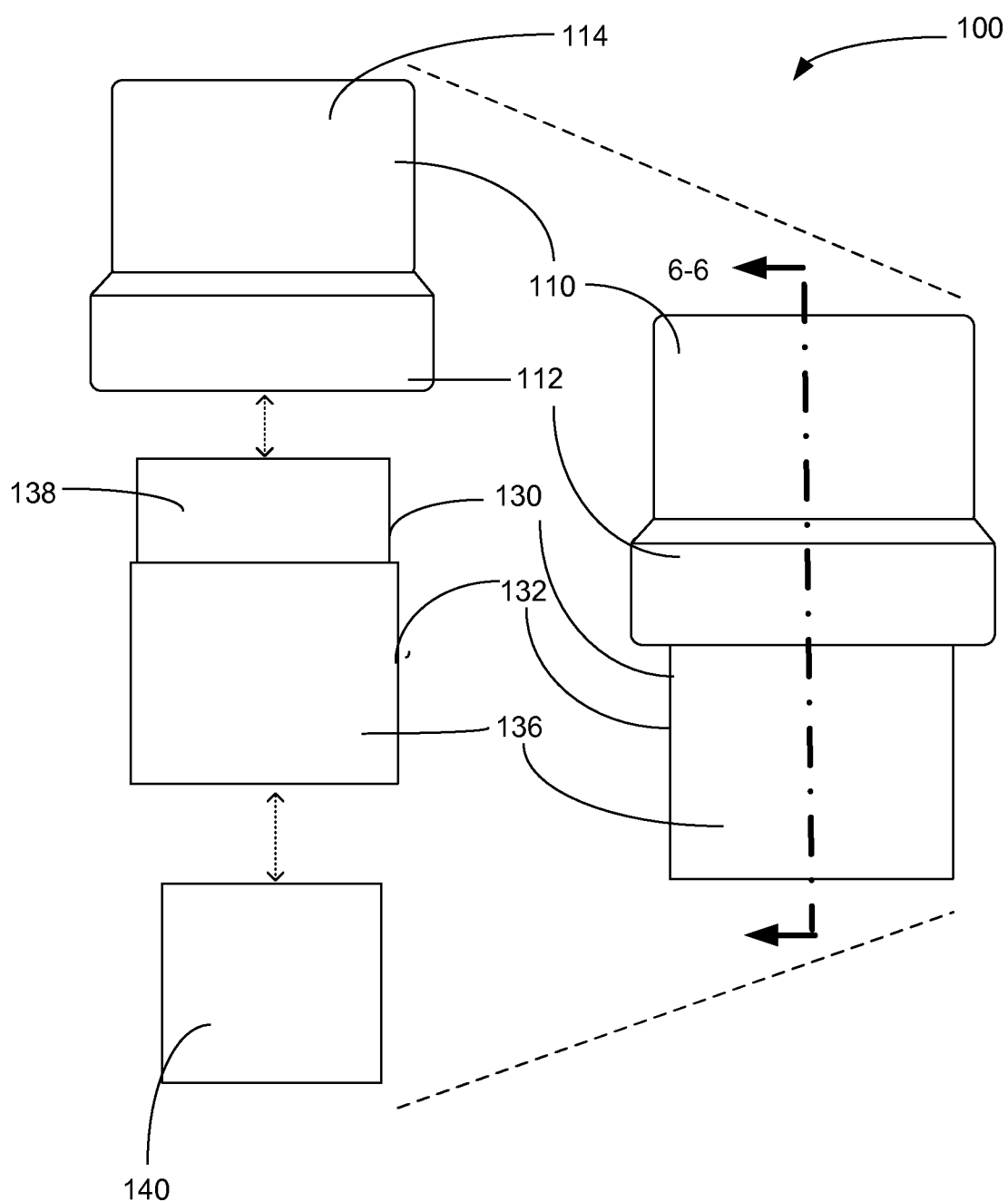
FIG. 5 shows an exploded view of the scent delivery adaptor of FIG. 1.
Figure 6:
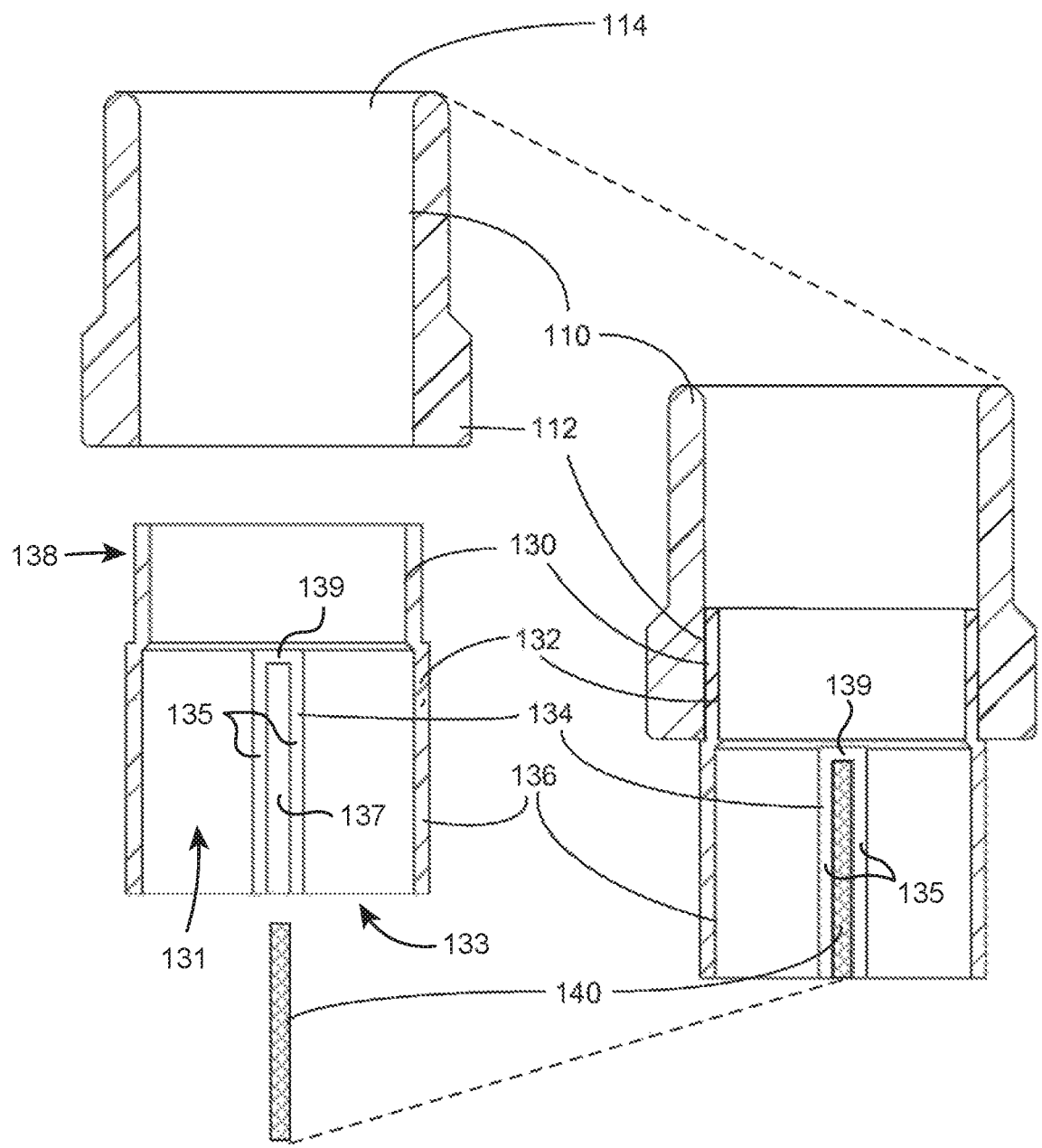
FIG. 6 shows a cross-sectional exploded view of the scent delivery adaptor as shown in FIG. 5.

Adaptor 100 may be formed such that it provides intermediate connections that work with existing hose and mask connectors. Adaptor 100 may be placed anywhere in the air supply conduit between the CPAP air generator 40 and the user, usually consisting of a hose 20, various connectors and swivels (not specifically identified), and the mask 10. In the illustrated embodiments, adaptor 100 may be placed at any connector point in the air supply conduit. The particular parts and functions of the illustrated embodiments are shown in FIGS. 5 and 6 and will be described hereafter.

Adaptor 100 may include mask connector 110 to connect adaptor 100 and with a swivel or inlet in mask 10. Mask connector 110 may provide a similar geometry and form as a standard end of hose 20, which is designed to couple with mask 10. Mask adaptor 110 may include a mask connection end 114 and a diffuser connection end 112. Mask adaptor 110 may be generally a tubular shape with appropriate inside diameters to accommodate coupling the inlet of mask 10 with the upper end 138 of hose connector 130. Mask connector 110 may be made of a pliable material such as rubber, silicone, vinyl, or other suitable material, which allows for a removable and secure press-fit with the other components.

Hose connector 130 may provide the housing for pad 140. Hose connector 130 may generally be a tubular shape and may include body 132, upper end 138 sized to cooperatively fit within the inner diameter of diffuser connection end 112 of mask connector 110, lower end 136, providing a connection point for hose 20, and slot 134 to hold pad 140 within the airstream of a CPAP machine. The outer diameter of lower end 136 may be sized and formed into a similar shape as the inlet of mask 10 such that hose 20 may connect to hose connector 130 in a similar way as it would connect with mask 10 without the need for modifying hose 20.

Slot 134 may be formed in the inner walls of body 132 either by forming a slot into the sidewalls or, as is shown in the Figures, by providing flanges 135 along opposing sidewalls sized to allow placement of pad 140 within the airway. For example, as shown in FIG. 4, each slot 134 is defined by two flanges 135 extending from the interior sidewall to form a U-shaped channel 137 that opens toward the lumen 131 of the hose connector 130. As shown in the longitudinal cross section of FIG. 6, the U-shaped channel 137 of slot 134 extends longitudinally from an opening 133 of the lower end 136 of the hose connector 130 to terminate at a channel block 139 disposed within the hose connector 130. As shown in FIG. 6, the channel block 139 joins the flanges 135 and prevents further advancement of the pad 140 within the U-shaped channel 137.

Hose connector 130 may be formed of any suitable material, to securely hold pad 140 (or similar) and connect effectively with hose 20 and mask connector 110 or directly to mask 10, depending on the particular configuration.

Additionally, any portion of adapter 100 may be formed of material resistant to the corrosive effects of essential oils. One principal function of adaptor 100 is to hold a suitable media within the airstream of a CPAP machine to provide diffusion and deliver of aromatic agents to a user of the CPAP machine.

Pad 140 may be formed of natural or polyester felt, cotton, paper, or any suitable media for holding and delivering a desired aromatic agent. Indeed, in some embodiments, replacement pads 140 may be available pre-loaded with a desirable aromatic or therapeutic agent, such as an essential oil, such that a user simply inserts a new pad 140 before each use. Or in other embodiments, a new amount of aromatic agent may be applied when desired, and the pad may be rinsed or simply reused if the same agent is to be used.

As will be apparent to those skilled in the art in which the invention is addressed, the present invention may be embodied in forms other than those specifically disclosed above without departing from the spirit or potential characteristics of the invention. Particular embodiments of the present invention described above are therefore to be considered in all respects as illustrative and not restrictive. The scope of the present invention is as set forth in the appended claims and equivalents thereof rather than being limited to the examples and embodiments contained in the foregoing description.

What is claimed is:

1. An adaptor, the adaptor comprising:
   a connector body, comprising a material resistant to corrosive effects of essential oils;
   a pair of slots disposed within a lumen of the connector body, each slot comprising two flanges extending from an interior sidewall of the connector body, forming a U-shaped channel that opens towards the lumen, and a channel block extending from the interior sidewall of the connector body, the channel block being disposed between the two flanges;
   a substantially planar diffuser pad disposed between and secured by the pair of slots; and
   at least one coupling mechanism on the connector body for coupling the connector body to a portion of a CPAP machine such that an airflow of the CPAP machine flows through the connector body and over both sides of the diffuser pad.

2. The adaptor of claim 1, wherein the adaptor is configured to couple directly to a CPAP mask.

3. The adaptor of claim 1, wherein the adaptor is configured to be placed in the airflow between an air generator and a mask of the CPAP machine.

4. The adaptor of claim 3, wherein the adaptor is configured such that when used with a CPAP machine, no modification of the existing CPAP hose, machine, or mask is required.

5. The adaptor of claim 1, further comprising essential oils permeated into the pad.

6. The adaptor of claim 1, wherein the pad is formed of polyester felt.

7. The adaptor of claim 1, wherein the connector body includes a hose connector and a mask connector.

8. The adaptor of claim 1, wherein the at least one coupling mechanism includes a tube formed of a pliable material.

9. The adaptor of claim 1, wherein each U-shaped channel extends longitudinally within the lumen from an opening of a lower end of the connector body and terminates at the channel block.

10. The adaptor of claim 1, wherein the channel block joins the two flanges and prevents further advancement of the substantially planar diffuser pad within the U-shaped channel.

11. A method of diffusing aromatic agents into the air supply of a CPAP machine, the method comprising:
   providing a CPAP machine having an air generator, a supply hose, and a mask;
   inserting the adaptor of claim 1 between the air generator and the mask, wherein the substantially planar diffuser pad is impregnated with aromatic agents.

12. The method of claim 11, further comprising impregnating the pas with the aromatic agents prior to using the CPAP machine.

13. The method of claim 11, wherein the adaptor is placed between the hose and the mask.

14. The method of claim 11, wherein the aromatic agents are essential oils.

15. The method of claim 14, wherein the pad is held within the airflow between the air generator and the mask by the adaptor.

16. A CPAP system, comprising:
   a CPAP machine having an air generator, a supply hose, and a mask; and
   the adaptor of claim 1.

17. The system of claim 16, wherein the adaptor is configured to couple directly to the CPAP mask.

18. The system of claim 16, wherein the adaptor is configured to be placed in the airflow between an air generator and a CPAP mask.

19. The system of claim 16, further comprising essential oils permeated into the diffuser pad.

20. An adaptor for delivering diffused aromatic agents, the adaptor comprising:
   a hose connector formed of a material resistant to corrosive effects of essential oils, the hose connector comprising:
      an outer diameter sized and shaped to fit an inner diameter of an existing hose of a CPAP machine;
      a diffuser section comprising an upper end, a lower end, a lumen defined by an inner surface of the diffuser section, and a pair of slots disposed within the lumen, wherein each slot comprises:
         two flanges extending from the inner surface of the connector body, forming a U-shaped channel that opens towards the lumen; and
         a channel block extending from the interior sidewall of the connector body and disposed between the two flanges,
      wherein the pair of slots is configured to hold a substantially planar diffuser pad within the lumen of the diffuser section such that an airflow of the CPAP machine flows over both sides of the diffuser pad; and
   a coupling mechanism formed of a pliable material and attached to an upper collar of the hose connector, wherein the coupling mechanism is sized and shaped to couple to an existing component of the CPAP machine and comprises an outer diameter that is greater than the outer diameter of the hose connector.

\* \* \* \* \*